United States Patent [19]

Marques

[11] Patent Number: 4,928,528
[45] Date of Patent: May 29, 1990

[54] ARTERIAL/VENOUS SIMULATOR

[75] Inventor: Jose A. Marques, Miami, Fla.

[73] Assignee: Cordis Corporation, Miami, Fla.

[21] Appl. No.: 223,868

[22] Filed: Jul. 25, 1988

[51] Int. Cl.⁵ ............................................. G01M 3/28
[52] U.S. Cl. ........................................................ 73/40
[58] Field of Search .................................. 73/40, 49.2

[56] References Cited

U.S. PATENT DOCUMENTS

| | | | |
|---|---|---|---|
| 2,874,566 | 2/1959 | Mastak | 73/40 |
| 3,546,923 | 12/1970 | Fletcher et al. | 73/40 |
| 3,827,283 | 8/1974 | Lerner et al. | 73/40 |
| 4,000,739 | 7/1975 | Stevens | 128/214.4 |
| 4,364,261 | 12/1982 | Askwith et al. | 73/40 |

Primary Examiner—Michael J. Tokar
Assistant Examiner—Joseph H. Roskos
Attorney, Agent, or Firm—Henry W. Collins; Thomas R. Vigil

[57] ABSTRACT

The treating device for testing the sealing strength of a seal in a catheter sheath introducer comprises a port for receiving the introducer, a mechanism for supplying pulsating liquid to the inside of the introducer, and controls for controlling the upper and lower pressures of the fluid supplied to the introducer while observing the sealing strength of the seal, with or without an elongate, rod-like member received therein. The method for testing the sealing strength of the fluid seal within a catheter sheath introducer including the steps of providing a port for engaging said introducer; engaging the introducer to the port in a fluid tight manner; supplying a pulsating flow of fluid to the inside of the introducer; controlling the upper and lower pressure parameters for the flowing fluid; and observing the seal for leakage.

18 Claims, 3 Drawing Sheets

ARTERIAL/VENOUS SIMULATOR

BACKGROUND OF THE INVENTION

1. Field of the Invention

The present invention relates to a testing device for assuring the sealing strength of fluid seals, such as those formed by gaskets provided in a passage within a sheath introducer for a catheter.

2. Description of the Prior Art

Heretofore, the sealing strength of fluid seals, such as those formed by gaskets provided in a passageway through a catheter sheath introducer, as disclosed in the Stevens U.S. Pat. No. 4,000,739 for Hemostasis Cannula, the teachings of which are incorporated herein by reference, has not been tested in an environment outside of actual use of the introducer.

The testing device of the present invention provides a means for testing the sealing strength of primary seals, as well as testing the sealing strength of secondary seals, of sheath introducers, prior to their actual use, as will be described in greater detail hereinafter.

SUMMARY OF THE INVENTION

According to the invention there is provided a testing device for testing the sealing strength of a seal in a catheter sheath introducer comprising:
 means for receiving the introducer;
 means for supplying pulsating liquid to the inside of the introducer; and
 means for controlling the upper and lower pressures of the fluid supplied to the introducer while observing the sealing strength of the seal, with or without an elongate, rod-like member received therein.

Further according to the invention there is provided a method for testing the sealing strength of a fluid seal within a catheter sheath introducer including the steps of:
 providing means for engaging said introducer;
 engaging said introducer to said engaging means in a fluid tight manner;
 supplying a pulsating flow of fluid to the inside of the introducer;
 controlling the upper and lower pressure parameters for the flowing fluid; and
 observing the seal for leakage.

DESCRIPTION OF THE PREFERRED EMBODIMENT

Figure 1:
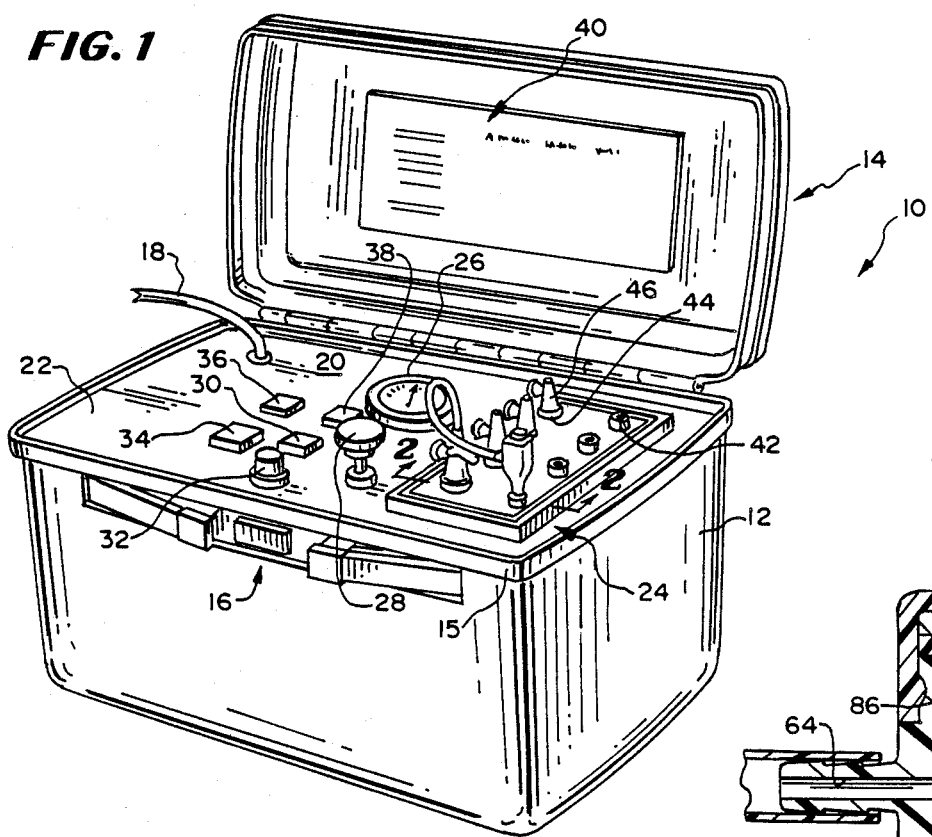
FIG. 1 is a perspective view of the arterial/venous simulator of the present invention and shows the casing and control panel thereof.

Referring now to the drawings in greater detail, there is illustrated in FIG. 1 a testing device for testing the sealing strength of fluid seals within a catheter sheath introducer, which comprises an arterial/venous simulator 10.

The device or simulator 10 is self-contained within a case or casing 12 having a pivotable fold down lid 14 which may be locked onto an upper rim 15 of the case 12 by latch means 16.

The simulator 10 is electrically powered and is provided with an electrical power cord 18, for operation by standard 110 volt AC current.

Figure 4:
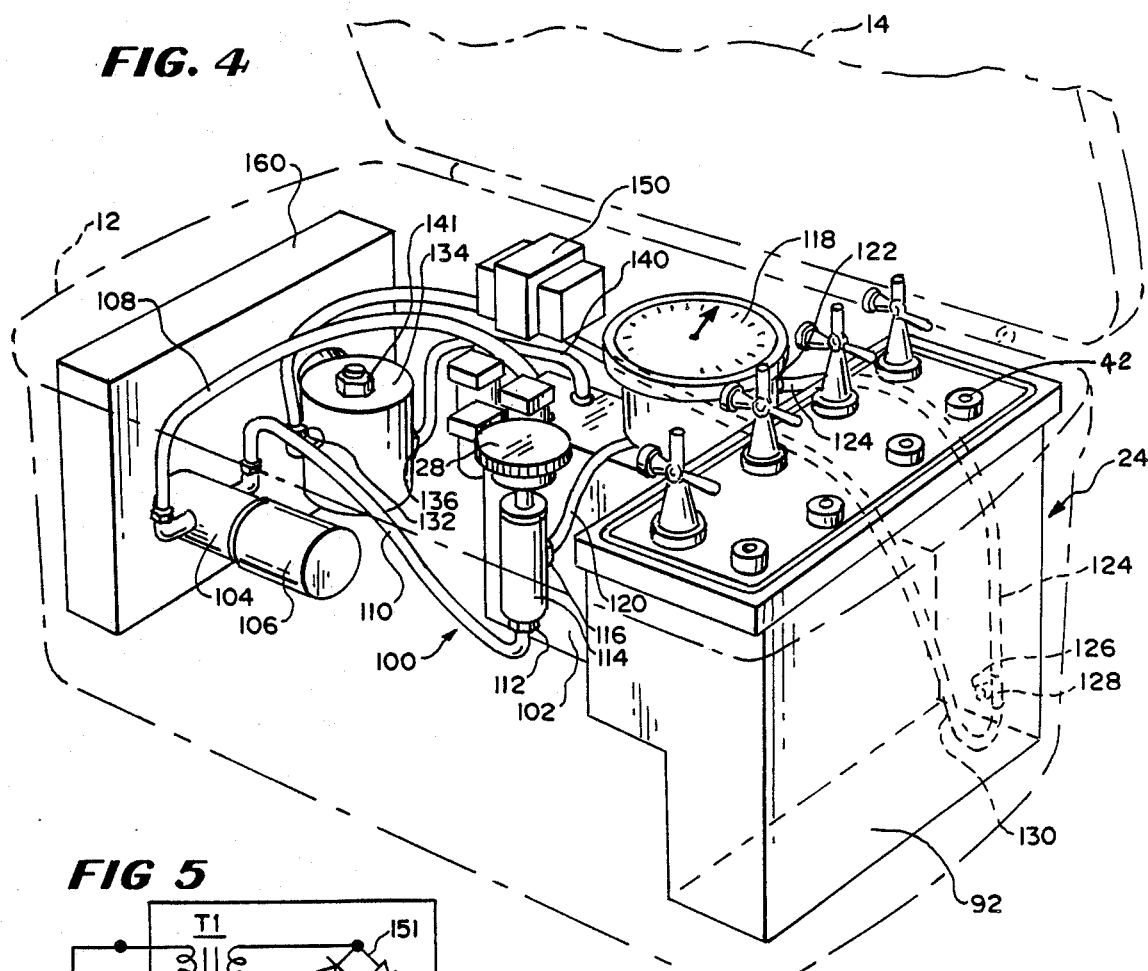
FIG. 4 is a perspective view into an interior compartment of the simulator, with the casing thereof shown in phantom, and shows the components of the simulator within the casing.

A control panel 20 of the simulator 10 forms a top or upper surface 22 for the case 12 and is removable from within the case 12 to allow access to components of the simulator 10, within the case or casing 12 (FIG. 4).

The control panel 20 includes a manifold section 24, which will be defined in greater detail hereinafter. A pressure gauge 26, which indicates the relative position of a pressure regulating valve 114 (FIG. 4) controlled by a rotatable knob 28 is also provided. There is further provided a switch 30 for turning a motor 106 (FIG. 4) of the simulator 10 on and off and a second rotatable knob 32 is provided for regulating the speed of the motor.

A power switch is provided for turning the simulator 10 on and off and, for safety sake, to protect the electrical circuitry of the simulator 10 from being shorted out by misuse or the like, two fuses 36 and 38, are provided. The fuse 36 is provided to protect the AC circuitry and the fuse 38 is provided to protect the DC circuitry of the simulator 10.

The gauge 26 measures pressure in psi and a conversion chart 40 for converting psi to mm Hg may be provided in the cover 14 for the simulator 10 for the sake of convenience.

Figure 2:
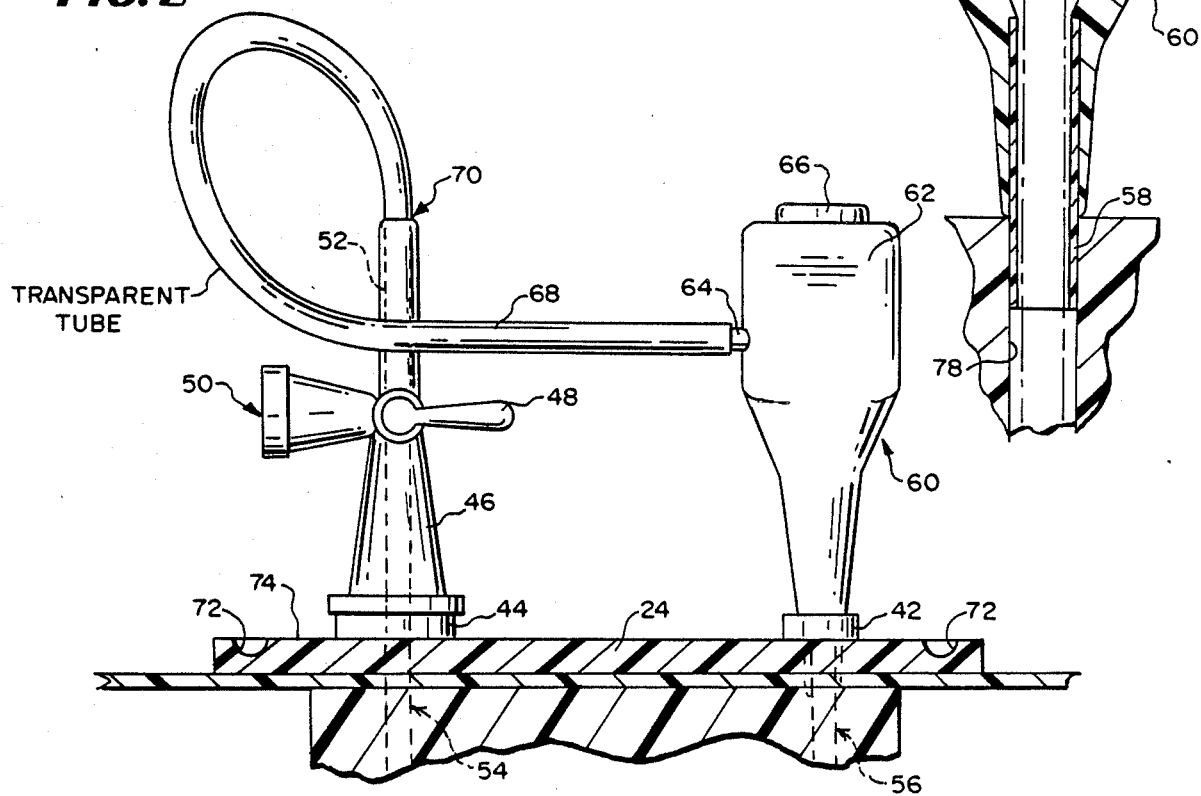
FIG. 2 is a side view, partly in section, of a catheter sheath introducer to be tested installed within a manifold of the simulator and is taken along line 2—2 of FIG. 1.

Turning now to FIG. 2, there is shown therein an enlarged view of one outflow port 42 and its corresponding drain port 44 of the manifold section 24, with the manifold section 24 therebeneath shown in cross-section.

The manifold section 24 is provided with a plurality of outflow ports 42, each of which coacts with a corresponding drain port 44, each drain port 44 being fitted with a manually manipulatable stopcock valve 46.

The stopcock valve 46 has a handle 48 which controls the flow of fluid through the valve 46. In this respect, the valve 46 has an auxiliary side port or channel 50 which may be opened by moving the handle 48 to close off a main or vertical channel 52 (shown in phantom). During use of simulator 10, the handle 48 should be vertically disposed to close off the side port 50 and maintain the main channel 52 open.

It is to be noted that, for the sake of compactness of the simulator 10, the valve 46 may be removable and may be engageable over and onto the drain port 44 in any known manner so long as the engagement is airtight.

The drain port 44 serves as a terminal connector 44 for a water return system 54, a portion of which is shown in phantom.

Turning now to the outflow port 42, the port 42 serves as a terminal connector 42 for a water supply system 56, a portion of which is shown in phantom.

The outflow port 42 is sized and configured to receive therein, in an airtight manner, an entrance tube 58

(FIG. 3) of a catheter sheath introducer 60, such as the Hemostasis Cannula disclosed in U.S. Pat. No. 4,000,739, the teachings of which are incorporated herein by reference. The introducer 60 also includes a body portion 62 having a lateral side port 64. Since the introducer 60 is designed for accepting a tubing or catheter therethrough, it also has a catheter port 66 therein, as will be described in greater detail in connection with the description of FIG. 3.

In use of the simulator 10, for testing the sealing strength the gaskets or seals (FIG. 3) of the sheath introducer 60, the side port 64 of the introducer 60 is connected via a clear tubing 68, to an inlet port 70 of the valve 46 in an airtight manner.

Since the simulator 10 involves transport of a fluid, and since the components of the simulator 10 are electrical, in case of a fluid buildup in the manifold section 24, an overflow channel 72 is provided in an upper surface 74 of the manifold section 24. It is to be understood that the overflow channel 72, communicates with the water return system 54, although such communication is not shown.

Figure 3:
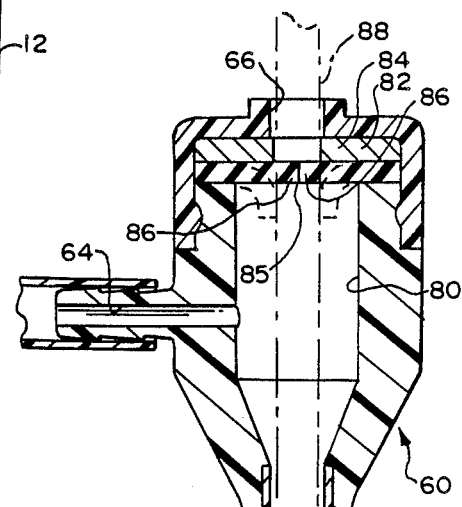
FIG. 3 is a cross-sectional view through an introducer being tested and a portion of the manifold.

Turning now to FIG. 3, there is shown therein an enlarged sectional view through the introducer 60 which is to be tested for sealing strength, using the simulator 10 of the present invention.

As shown, the entrance tube 58 of the introducer 6 fits, in an airtight manner into a throughbore 78 of the outflow port 42. The interior of the tube 58 communicates with a primary flow path or channel 80 through the introducer 60. The side port 64 in the body 62 of the introducer 60 also communicates with the primary channel 80.

Since a single direction of flow through the introducer 60 is necessary, a primary seal 82 and a second seal 84 are provided around a catheter, tube, dilator or test rod/stylist 88 received in the introducer 60 above; the primary channel 80 at a position just internal to the catheter port 66.

The primary seal 82 is formed by a gasket 82 having a central slit 85, which in the introducer 60 is in the form of the hemostasis cannula 60 shown, is Y shaped and sections 86 formed in the seal 82 around and between branches of the slit 85, upon insertion of a catheter, or in the case of testing of the second seal 84, upon insertion of a stiff plastic tube or vessel dilator 88 (shown in phantom) having an outer diameter equal to an outer diameter of a catheter to be utilized with the introducer 60, flex inwardly (as shown in phantom) and rest against the tube 88.

The secondary seal 84, as shown, seals against the tube 88 to prevent leakage through the port 66 when the tube 88 is received within the primary channel 80 of the introducer 60. If the tube 88 is used, a Luer-lock type cap (not shown) should be engaged over the end of the tube extending outwardly of the introducer 60.

In order to assure sealing strength of the seals 82 and 84, they must be tested under conditions similar to those in the human body. The arterial/venous simulator 10 of the present invention provides such conditions, considered critical for testing.

The simulator 10, as shown in FIG. 4, with the case or casing 12 and cover 14 illustrated in phantom, includes electrical circuitry (FIG. 5) and fluid circuitry (FIG. 6) which work together to provide a pulsating flow of fluid such as that encountered in the circulating system of the human body, to and through the introducer 60 to test the sealing strength of the seals 82 and 84 as will be defined hereinafter.

FIG. 4 shows a layout of the internal components of the simulator 10 and their arrangement within the case 12. For the sake of clarity, the electrical connections of the electrical circuitry have been left out and will be described in detail in connection with the description of FIG. 5.

In FIG. 4 the control panel 20 also has been left off.

Turning first to the manifold section 24, there is provided therein four pairs of ports, each pair including an; outflow port 42 and corresponding drain port 44 The manifold section 24 includes an inverted L shaped fluid directing manifold 92 therebeneath which will be described with reference to FIG. 6.

Since the simulator 10 includes a fluid circuit or system 100 (FIG. 6), a water storage tank 102 is necessary. Also, to produce a flow of fluid or water through the system 100, a pump 104 and a motor 106 for driving the pump 104 are necessary. Water from the tank 102 is supplied to the pump 104 via a line 108. The water exiting the pump 104 is supplied via a line 110 to an inlet port 112 of a pressure regulating valve 114. The knob 28 on the panel 20 may be rotated to control the pressure at which the water exits an outlet port 116 of the valve. To provide means for monitoring the pressure of the water exiting the valve 114, the pressure gauge 26, which measures pressure in psi, is connected via a line 120 to the outlet port 116 of the valve 114.

The valve 114 is provided for regulating the fluid pressure, within a range between 1 and 10 psi, for the fluid system 100. By using the conversion table 40 provided in the cover 14 of the simulator 10, the 1 to 10 psi of pressure can be converted to mm Hg, the parameter for measuring circulatory fluid pressure in the human body, with the range of 1 to 10 psi encompassing a range between approximately 50 and 520 mm Hg. The need for such regulatability will be discussed later.

The water or fluid then exits the gauge 26 at 122 and is supplied via a line 124 and port 126 to a fluid pathway 202 (FIG. 6) within the fluid directing manifold 92 of the manifold section 24. The port 126, by using a T connector 128 therewith, serves as an inlet/outlet port 126 for the fluid directing manifold 92.

Fluid exiting via the inlet/outlet port 126 is supplied via a line 130 to an inlet port 132 of an adjustable orifice valve 133 incorporated in a solenoid 134 of the system 100. The valve 133 of the solenoid 134 also has an outlet port 136. Fluid exiting the solenoid outlet port 136 is returned via a line 140 to the tank 102.

The valve 133 in the solenoid 134 is of an adjustable orifice type and has an intermittent mode of operation and provides a pulsatile fluid flow through the fluid system 100. In this respect, the pressure deviation created by the intermittent mode of operation, or opening of the valve orifice, works negatively against the pressure of the fluid flow, and intermittently decreases the pressure of the fluid flow, in a pulsating manner, to create a fluid stream which has intermittent high and low pressure pulses therein, simulating blood pressure readings, which are pulsatile, in the human body. The size of the orifice in the valve 133 may be varied by adjusting the position of a nut 141 (FIG. 4) of the solenoid 134 to adjust the degree of orifice opening. Thus, the simulator 10 is capable of simulating a controllably adjustable pulsatile fluid flow corresponding to arterial/venous flow in a circulatory system of a human body.

The provision of such a pulsatile fluid flow in the fluid system 100 of the simulator 10 allows for testing of the seals 82 and 84 of the introducer 60 under conditions which simulate the pulsatile flow of blood in the body of a patient, thus making the testing procedure parameters almost identical to those which will be encountered when the introducer 60 is utilized, such as when utilized as an introducer for intravascular catheters, such as those used in angiography, or for catheters used in association with a procedure such as heparin drip or saline flush.

Figure 5:
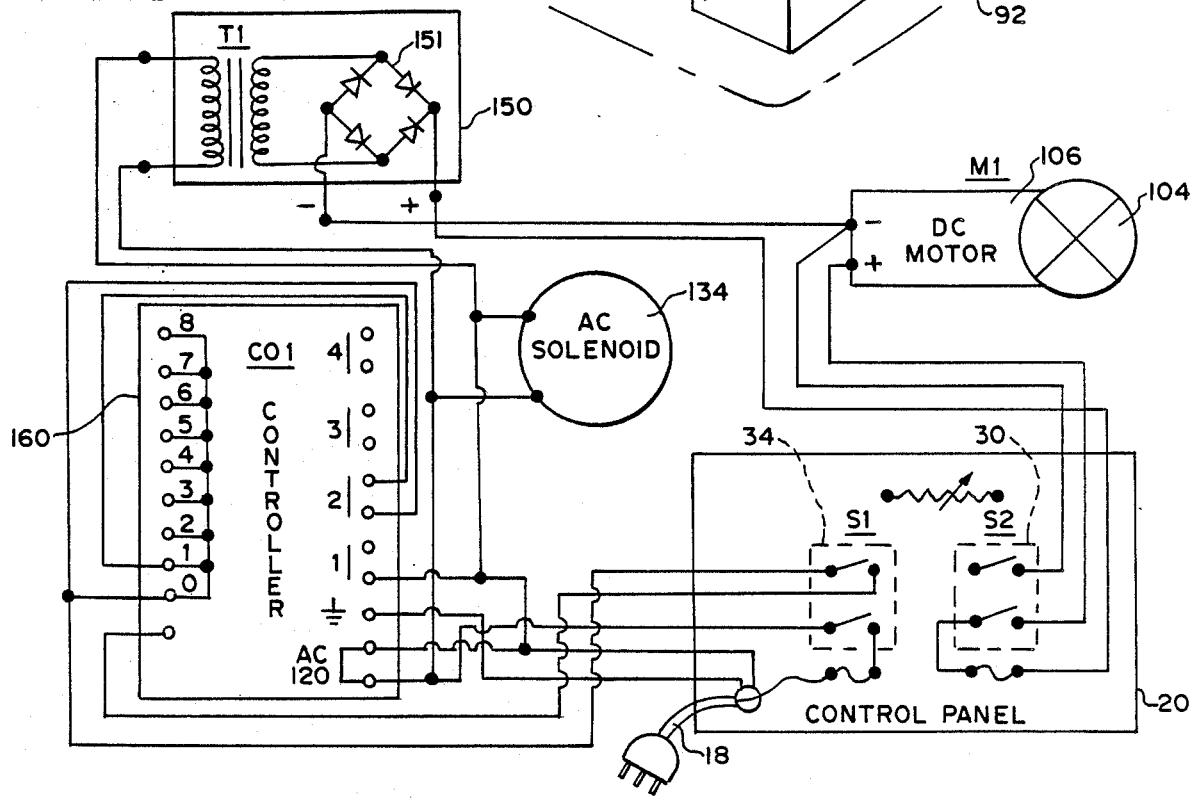
FIG. 5 shows a block schematic diagram of the electrical circuitry of the simulator.

As shown in FIG. 5, the simulator 10 includes a power supply 150 for converting 110 volt AC current into a 12 volt DC current. The simulator 10 is supplied with a standard 110 volt AC current via the power cord 18.

The electrical circuit for the simulator 10 is shown in FIG. 5 and includes a power supply 150 which includes a transformer T1 and a rectifier 151 for supplying direct current to the DC motor 106 for the pump 104. The AC cord 18 is connected through the switch 34 to the power supply 150, to a programmable controller 160, and to the AC solenoid 134. The switch 30 controls energization of the DC motor 106. The switches 30 and 34 can be operated separately or ganged together and operated together.

Figure 6:
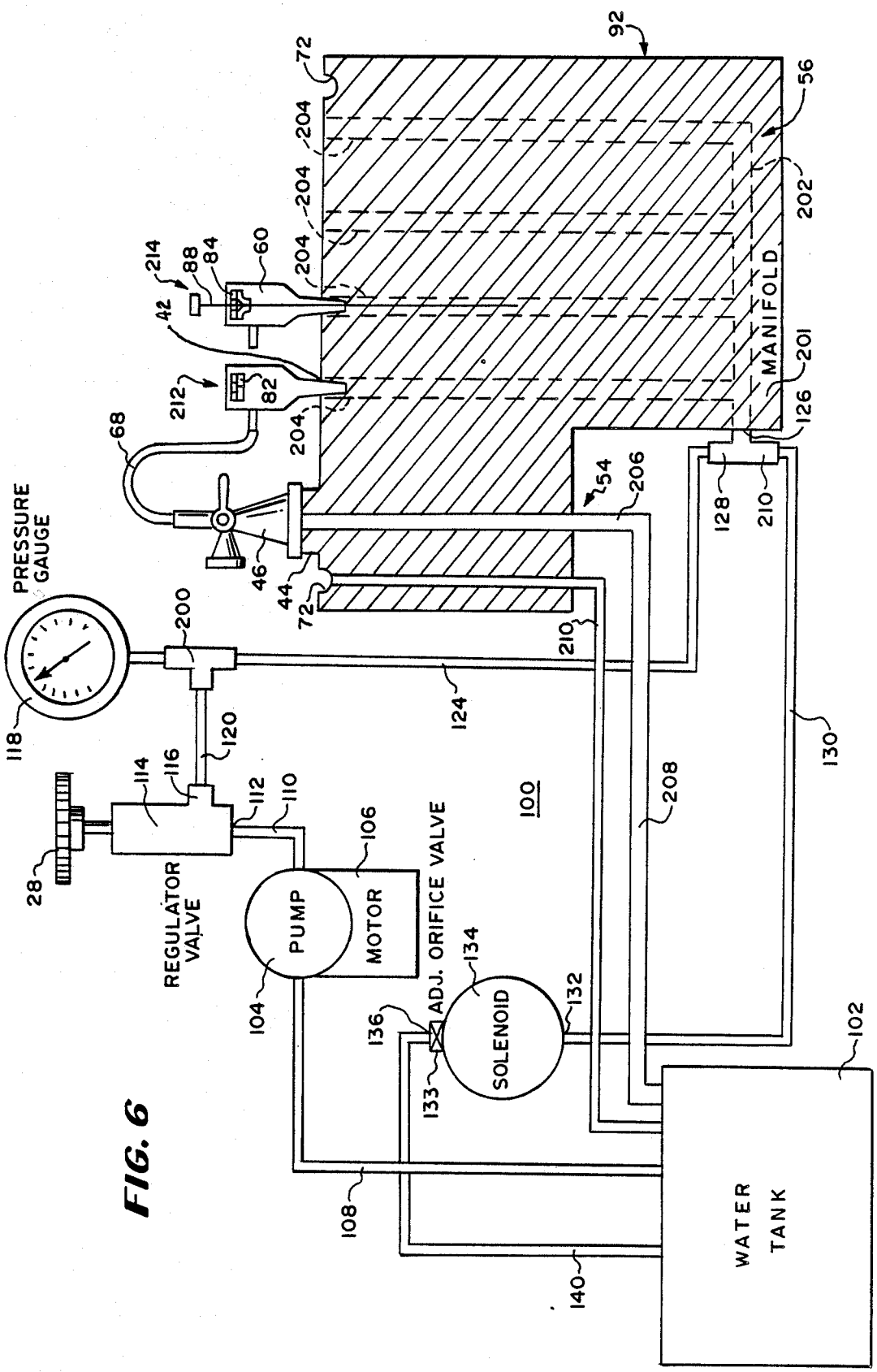
FIG. 6 is a block schematic diagram of the fluid circuitry of the simulator.

FIG. 6 shows a block schematic diagram of the fluid circuit or system 100 of the simulator 10. As shown, water from the water tank 102 is carried to the pump 104, run by the motor 106, through or via the water supply line 108.

It is to be understood that the speed of the motor 106 is adjustable by adjusting the position of the motor speed adjustment knob 32 (FIG. 1) on the panel 20. The water is pumped by the pump 104 via the conduit 110 into the inlet port 112 of the pressure regulating valve 114 which can be adjusted by rotating the pressure regulating knob 28 on the control panel 20 until a desired fluid pressure is reached in the fluid circuit 100.

In order to monitor the pressure of the fluid in the system 100, the pressure gauge 26 is incorporated into the system 100 and is connected via the line 120 (FIG. 6), through suitable means, such as a T connector 200, to the outlet port 116 of the valve 114. The fluid then continues via the line 124 to the T connector 128, which provides an inlet/outlet function for the port 126, in a lowermost area 201 of the fluid directing manifold 92, illustrated in cross-section.

As shown, the port 126 communicates with a main fluid channel 202 which supplies fluid to a plurality of secondary or feeder channels 204. These feeder channels 204 form the water supply system 56 which is used in testing the sealing strength of the seals 82 and 84 and which supplies water to each of the multiple outflow ports 42, illustrated in detail in FIGS. 2 and 3.

The directing manifold 92 further incorporates the water return system 54, a portion of which is shown in FIG. 2.

The water return system 54 includes a plurality of secondary water return channels 206 each of which forms a continuation of a drain port 44 of a particular stopcock valve 46, although only one such port 44 is illustrated.

A primary water return conduit 208 is incorporated in the water return system 54 to transport water from the secondary water return channels 206 to the water tank 102. The primary conduit 208 further may be used to assist in draining water which may accumulate in the overflow channel 72 of the manifold section 24, although not shown. Alternatively, as shown in FIG. 6 a separate overflow conduit 210 may be provided directly linking the overflow channel 72 and the tank 102.

The fluid system 100 may be considered as functional at this point.

However to simulate the pulsatile circulatory flow in a human body, a pulsatile fluid flow must be provided through the system 100.

To accomplish this, the solenoid 134 incorporating the adjustable orifice valve 133 must be incorporated into the system 100.

As shown, the T connector 128 connected to the inlet/outlet port 126 has a branch or leg 210 thereof connected via conduit 130 to an inlet 132 of the solenoid controlled valve 133. An inlet 136 of the valve 133 communicates with the water tank 102 via conduit 140, forming, when the introducer 60 is mounted as shown at 212 in FIG. 6, a closed fluid circuit 100 which has fluid pulsing therethrough.

The valve 133 is preferably set to provide a throttled pressure which corresponds to a minimal human circulatory (diastolic) pressure, in the area of 80 mm Hg, when actuated and allowing the pressurized fluid to escape therethrough to cause a pressure drop in the system 10, to approximately 80 mm Hg.

Control of the solenoid 134 is provided via the controller 160 as described in connection with the description of FIG. 5.

In use of the simulator 10 for testing the sealing strength of the seals 82 and 84, one first must be sure that the simulator 10 is set up for operation. In this respect, a user will first install each of four introducers 60 to be tested into four ports 42 illustrated with the side port 64 of each introducer 60 extending in the direction of the corresponding drain port 44. Next, the stopcock valves 46, if not already connected to the outlet ports 44, must be engaged thereto and the stopcock handle 48 on each valve 46 must be rotated to a vertical position to close the side port 64 of each stopcock valve 46 and open the through port 52 therein.

Next, side port 64 of each of the introducers 60 is connected to an upper end or inlet opening 70 of each of the respective stopcock valves 46, which are seated over the corresponding drain ports 44, by the clear tubing 68, to form the closed fluid circuit 100. Next, the power switch 34 of the simulator 10 is switched on, as is the motor switch 30, to begin operation of the DC motor 106 which drives the pump 104. While the motor 106 is running for the first several seconds, the user observes the tubing 68 to identify air bubbles flowing outwardly into the tubing 68 from the introducer side port 64.

The presence of air bubbles, if such presence is not eliminated within the first few seconds of operation of the motor 106, may indicate that the level of water in the water tank 102 is low. The method of checking the level of water in the tank 102 and the method for injecting water into the tank 102 will be described below.

If, on the other hand, the air bubble appear to be purged from the system 100 within the first few seconds of operation of the motor 106, testing of the sealing strength of the seals 82 and 84 of the introducer 60 may be performed.

The first step in performing the seal testing is to set a desired upper range limit for the pressure of the water flowing through the system 100 by rotating the knob 28 controlling the regulating valve 114. The recommended range in psi for testing is between 2 and 6 psi and, using the pressure gauge 26 to identify the pressure of the fluid, the user may turn the knob 28 clockwise to decrease the pressure of the fluid within the system 100 or counterclockwise to increase the pressure. It is to be noted that the regulating valve 114 should never necessarily be fully closed as such as closed condition may cause overheating of the motor 106. The motor speed control switch 30 may be provided with a signal light (not shown) which may be set to blink excessively to indicate an overheated condition of the motor 106 to warn the user to turn the motor 106 off and let same cool. Once the upper limit or level of the fluid pressure has been set by rotation of the pressure knob 28, the valve 133 of the solenoid 134 can have its orifice adjusted, such as by rotation of the nut 141 (FIG. 4) of the solenoid 134, to define or set the size of the valve orifice and thus set the lower limit of fluid pressure with the fluid in the system 100 intermittently exerting the set upper limit and then the set lower limit, to provide a pulsatile flow of the water trough the fluid system 100. Such lower limit may also be monitored by checking the pressure gauge 26.

In testing of the primary seal 82, as illustrated at 212 in FIG. 6, one merely observes the catheter port 66 of the introducer 60 to see if any water is being expelled therethrough, when the water tank 102 is in a filled condition. For ease in identifying the leakage of water, the water in the system 100 may be colored. The presence of such fluid or water will confirm that the primary seal 82, when in the closed position shown, is leaking and the user of the introducer 60 will be apprised of the leakage or defect in the seal 82 and will not use the introducer 60. Here the importance of the provision of the overflow channel 72 comes into play, for transporting any fluid or water leaking out of the introducer 60 back to the water tank 102, without overflowing the manifold portion 24 and possibly shorting out the electrical circuitry of the device 10.

Alternatively, for testing of the secondary seal 84 of the introducer 60, as shown at 214, a plastic tube, rod, stylet or dilator 88, having the same or similar diameter to a catheter which will be utilized with the introducer 60, can be fed into the introducer 60 through the catheter port 66 provided for receipt of the catheter causing a downward flexion of the sections 86 of the primary seal 82 against an outer surface of the tube or dilator 88, as shown in phantom in FIG. 3. When such a hollow dilator or tube 88 is used in testing the secondary seal 84, a top or upwardly extending end (not shown) of the dilator or tube 88 must be blocked, such as be engagement of a Luer-lock type cap (not shown) thereover, to keep the liquid or water of the system 100 from jetting outwardly therefrom.

Alternatively, when a solid body rod or stylet 88 having a minimum circumferential dimension is used to open the primary seal 82 a small degree and test for the sealing strength of the seal formed by the inwardly flexed portions 86 of the primary seal or gasket 82 against the stylet 88 as shown in FIG. 6 at 214, no cap is necessary. One, again, merely observes for water leaking from the catheter receiving port 66.

Turning now to the step of checking the level of the water in the tank 102, the control panel 20, as noted above, is not permanently mounted to the case 12 and so can be lifted up to provide access to the water tank 102. To lift the control panel 20 off the case 14, one grasps the regulator valve knob 28 in one hand and places the fingers of the left hand beneath the left edge of the panel 20. By slowing raising the left end of the control panel 20, the water tank 102 becomes visible. There are provided on the tank 102 indicia marking denoting "FULL" approximately halfway up the side of the tank 102.

If the water is below the "FULL" level, a syringe (not shown) supplied with the device 10 is filled with water and the water may then be injected into the tank 102, up to the "FULL" level by inserting a tip of the syringe into a fill tubing (not shown) which communicates with the interior of the tank 102 and injecting the water. Also, although not illustrated, to provide vent means for the tank 102, if desired, a vent port may be provided on the top surface of the tank.

After the tank 102 has been filled as described above, one merely lowers the panel 20 back into the case 12 and is ready to proceed further as described above.

As described above, the arterial/venous simulator device 10 of the present invention provides a simple means and method for using such means in testing of the sealing strength of primary and secondary seals or gaskets in a primary passage of a catheter sheath introducer.

The device and method for using same have a number of advantages, some of which have been described above and others of which are inherent in the invention. Also, various modifications can be proposed without departing from the teachings of the invention. Accordingly, the scope of the invention is only to be limited as necessitated by the accompanying claims.

I claim:

1. A testing device for testing the sealing strength of a seal in a catheter sheath introducer comprising:
   means for receiving the introducer;
   means for supplying pulsating liquid to the inside of the introducer; and
   means for controlling the upper and lower pressures of the fluid supplied to the introducer while observing the sealing strength of the seal, with or without an elongate, rod-like member received therein.

2. The device of claim 1 wherein said means for receiving the introducer comprise an outflow port of a fluid system which is adapted to engage therein, in a liquid tight manner, an entrance tube portion of the introducer.

3. The device of claim 2 including a fluid container.

4. The device of claim 1 wherein said means for supplying pulsating liquid comprise a closed fluid system.

5. The device of claim 4 wherein said closed fluid system includes pump means and a motor for operating said pump means.

6. The device of claim 5 wherein said closed fluid system further includes a regulatable pressure valve which is settable for providing a high pressure flow of fluid within the fluid system.

7. The device of claim 6 wherein said closed fluid system further includes a variable orifice solenoid valve which is intermittently actuatable to open and allow said high pressure fluid in said system to escape therethrough.

8. The device of claim 7 wherein the variable orifice valve has adjustment means engaged therewith which are operable to adjust the size of the orifice.

9. The device of claim 8 wherein said adjustment means are settable to provide a particular intermittent level of low pressure flow of the fluid within the system.

10. The device of claim 1 further including means for powering said device.

11. The device of claim 10 wherein said powering means include a transformer which is connected to an A.C. voltage source and which is operable to covert an AC voltage to a DC voltage.

12. The device of claim 11 wherein said powering means further include a rectifier.

13. The device of claim 10 including a solenoid for controlling liquid flow in said device, a programmable controller for controlling operation of said device and means for connecting said solenoid and said programmable controller to an AC voltage source.

14. The device of claim 13 including a variable orifice valve and said solenoid is coupled to said variable orifice valve for intermittently causing actuation of same.

15. The device of claim 13 wherein said programmable controller is coupled to said solenoid for controlling actuation of said solenoid for actuating said variable orifice valve.

16. A method for testing the sealing strength of a fluid seal within a catheter sheath introducer including the steps of:
   providing means for engaging said introducer;
   engaging said introducer to said engaging means in a fluid tight manner;
   supplying a pulsating flow or fluid to the inside of the introducer;
   controlling the upper and lower pressure parameters for the flowing fluid; and
   observing the seal for leakage.

17. The method of claim 16 further including the step of inserting an elongate rod like member through the seal.

18. A device for testing the sealing strength of fluid passageway seals of a catheter sheath introducer comprising:
   a fluid container;
   a closed fluid system including
   an outflow fluid pathway from said container;
   means for connecting the outflow fluid pathway to an entrance tube portion of the passageway in the introducer;
   a return fluid pathway to said container;
   means for connecting the return fluid pathway to a side port of the introducer;
   means for creating a flow of fluid through said system;
   means for causing pulsation of said fluid flow between a predetermined high level of fluid pressure and a predetermined low level of fluid pressure;
   means for regulating said high and low predetermined pressure levels; and
   means for supplying electrical current to said device.

* * * * *